Nov. 8, 1960 L. L. BROOKS Plant Pat. 1,983

AZALEA PLANT

Filed Nov. 3, 1959

L. L. Brooks Inventor

United States Patent Office

Plant Pat. 1,983
Patented Nov. 8, 1960

1,983

AZALEA PLANT

Lenard L. Brooks, Modesto, Calif.

Filed Nov. 3, 1959, Ser. No. 850,748

1 Claim. (Cl. 47—60)

My present invention relates to a new and distinct variety of azalea plant, such azalea plant being principally characterized by its habit of setting an unusual number of flower buds, its unusually heavy textured leaves, the ease with which it can be grown on its own roots, the ease with which it produces well shaped plants of very high forcing quality and the exceptional keeping quality of the distinctive flowers.

The instant variety is the result of a series of crosses between the kurume and indica type azaleas made in the experimental section of my nursery at Modesto, California. It was recognized by me as having exceptional qualities for commercial use, it was therefore taken for propagation by cuttings and the plants thus produced carried forward all the distinguishing characteristics of the parent plant. Subsequent propagation of the variety has shown that it is stable in all its novel characteristics. The original asexual reproduction by cuttings was carried out in the experimental section of my nursery at Modesto, California.

Referring now more specifically to the botanical details of the new and distinct variety of azalea plant, the following is a more detailed description of the same:

Plant:

*Form.*—Well branched, symmetrical, spreading.

*Growing habit.*—Dense and bushy with an abundance of large, dark green, heavy textured leaves.

*Blooming habit.*—Profuse, flowering evenly over the entire plant at the same time when forced in the greenhouse or flowered naturally in the garden. It flowers profusely as a one year old plant.

*Blooming season.*—Plants growing in the outdoor section of my experimental nursery at Modesto, California, bloom naturally in early April. It has exceptional qualities as a late greenhouse forcing variety.

Foliage:

*Size.*—Maximum size of mature leaves on thrifty young plants is about two and one half inches long and one and one quarter inches wide, each plant having many smaller leaves. As the plants attain age the average size becomes smaller.

*Color.*—Growing under good conditions, with an ideal pH value, the color of the mature leaves are a deep hemlock green, plate 32–H–12, lighter beneath. Young leaves lighter green.

*Shape.*—Broadly ovate, pointed.

*Aspect.*—Glossy and smooth.

*Texture.*—Heavy.

*Edge.*—Without serrations, some minute hairs.

*Ribs and veins.*—Normal.

Flower:

*Size.*—Two and one half to three inches.

*Borne.*—One to twenty on each stem. Strong branches often set up to eight or ten flower buds, each bud producing one to three flowers. Multiple bud setting constitutes one of the novel features in this variety.

Figure 1:
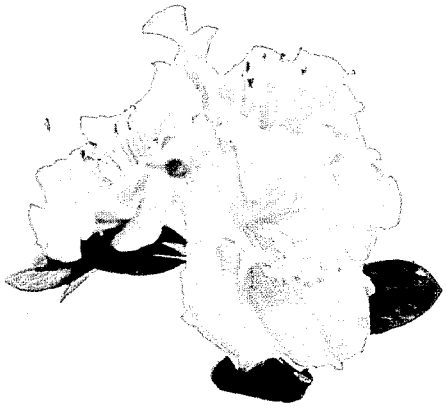
Fig. 1 is a perspective view of three flowers from a single bud.
Figure 2:
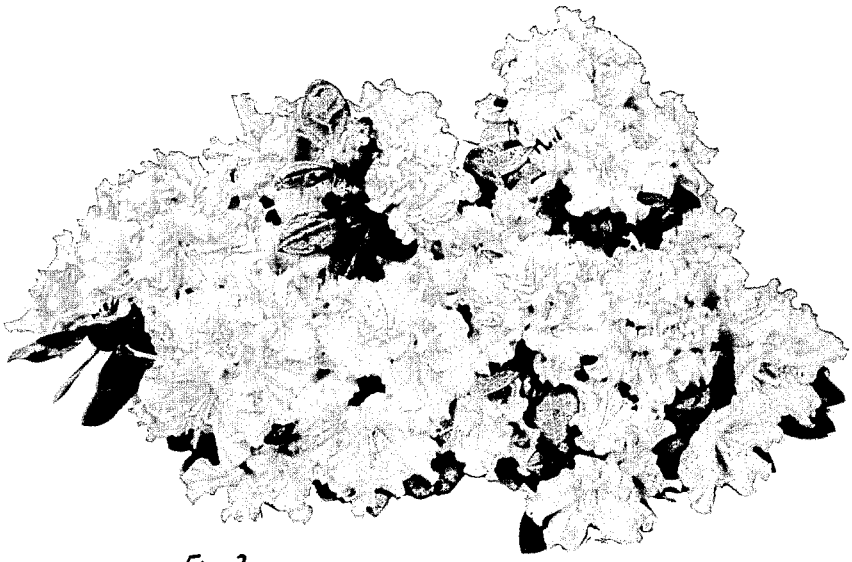
Fig. 2 is a perspective view of a plant in full flower.

*Form.*—Hose-in-hose, one flower set within the other. Often the outer hose does not develop fully. Rather than having normal stamens, the center of the flower is often composed of a widely varying number of petaloids in various shapes and sizes, and these are often antheriferous. Eleven anthers have been observed in one flower, ten being attached to petaloids, only one being attached to a filament in a normal manner. At times a small petaloid will develop at or near the upper end of a filament and these are nearly always white. This characteristic can be seen clearly in several flowers in Fig. 2, lower side.

*Permanence.*—Long lasting, retaining the colors well until the flowers are ready to fall.

*Color.*—Red (Plate 4–I–6), with orange tones at the base. Slight throat markings in a deeper shade.

Petals:

*Texture.*—Substantial.

*Arrangement.*—Normal for its type.

*Shape.*—Broadly ovate.

Reproductive organs:

*Stamens.*—Generally only one or two completely normal stamens develop in each flower. The anther is maroon.

*Pollen.*—White.

*Pistil.*—Often abnormal in shape. The style is about the same color as the petals. Stigma is a little deeper in color.

*Ovule.*—Usually but not always well developed.

All color plate identifications refer to "A Dictionary of Color" by Maerz and Paul.

Compared to other well known azaleas, this variety has some characteristics similar to Hexe (not patented), but is distinguished by the following principal differences:

(1) The plant grows slower and is much more compact in habit of growth and it produces many more flower buds.

(2) The foliage is a deeper green and the texture is much heavier.

(3) The flowers are a little larger and are less vase formed. The color is better because it has more of the orange shades.

Having thus described the invention, I claim:

A new and distinct variety of azalea plant substantially as herein shown and described, characterized particularly by its compact habit of growth, its deep green heavy textured leaves, its habit of setting many multiple flower buds, the abundance of the long lasting red flowers, its ease of reproduction by cuttings and its high value as a late greenhouse forcing and garden variety for mild climates.

No references cited.